United States Patent
DeTitta et al.

(10) Patent No.: US 6,368,402 B2
(45) Date of Patent: Apr. 9, 2002

(54) METHOD FOR GROWING CRYSTALS

(75) Inventors: George T. DeTitta, Kenmore; Joseph R. Luft, Tonawanda; Jennifer Wolfley, Orchard Park; Robert J. Collins, Buffalo, all of NY (US)

(73) Assignee: Hauptman-Woodward Medical Research Institute, Inc., Buffalo, NY (US)

(*) Notice: Subject to any disclaimer, the term of this patent is extended or adjusted under 35 U.S.C. 154(b) by 0 days.

(21) Appl. No.: 09/840,672

(22) Filed: Apr. 23, 2001

Related U.S. Application Data

(60) Provisional application No. 60/198,995, filed on Apr. 21, 2000.

(51) Int. Cl.$^7$ ............................................. C30B 28/00
(52) U.S. Cl. ........................... 117/68; 117/69; 117/937
(58) Field of Search ............................. 117/68, 69, 937

(56) References Cited

PUBLICATIONS

Jarmila Jancarik and Sung–Hou Kim, Sparse matrix sampling: a screening method for crystallization of proteins, Journal of Applied Crystallography (1991). 24, 409–411, Department of Chemistry and Lawrence Berkeley Laboratory, University of California, Berkeley, CA, USA.

Bob Cudney and Sam Patel, Screening and Optimization Strategies for Macromolecular Crystal Growth, Acta Cryst. (1994). D50, 414–423, University of California Riverside, Department of Biochemistry, Riverside CA, USA.

Imre Berger, Chulhee Kang, Nanda Sinha, Mark Wolters and Alexander Rich, A Highly Efficient 24–Condition Matrix for the Crystallization of Nucleic Acid Fragments, Department of Biology, Massachusetts Institute of Technology, Cambridge, MA, USA.

R. Michael Garavito, Crystallizing Membrane Proteins: Experiments on Different Systems, Chapter 4, pp. 89–105, H. Michel (Ed.) CRC Press.

Charles W. Carter, Jr., [5] Response Surface Methods for Optimizing and Improving Reproducibility of Crystal Growth, Methods in Enzymology, vol. 276.

Richard L. Kingston, Heather M. Baker and Edward N. Baker, Search Designs for Protein Crystallization Based on Orthogonal Arrays, Acta Cryst. (1994) D50, 429–440, Department of Chemistry and Biochemistry, Massey University, Palmerston North, New Zealand.

Huey–Sheng Shieh, William C. Stallings, Anna M. Stevens and Roderick A. Stegeman, Using Sampling Techniques in Protein Crystallization, Acta Cryst. (1995). D51, 305–310, Searle/Monsanto, BB4K, Department of Medicinal and Structural Chemistry, Chesterfield, MO, USA.

Madeleine Riès–Kautt and Arnaud Ducruix, [3] Inferences Drawn from Physicochemical Studies of Crystallogenesis and Precrystalline State, Methods in Enzymology, vol. 276.

(List continued on next page.)

*Primary Examiner*—Felisa Hiteshew
(74) *Attorney, Agent, or Firm*—Hodgson Russ LLP

(57) ABSTRACT

A high throughput crystallization methodology using 1,536 well microassay plate technology is described. The methodology uses mother-daughter plate technology with robotic control to deliver oil, unique crystallization cocktails, and a protein solution to each of the wells. This provides 1,536 unique microbatch crystallization experiments using as little as 6 mg of protein in 600 microliters of solution. The time required to deliver a protein solution to a prepared experiment plate is less than 10 minutes. A plate imaging system with a capacity of 28 microassay plates is also described. The imaging system digitally records the results of the experiments for later comparison to database results.

19 Claims, 4 Drawing Sheets

OTHER PUBLICATIONS

M.G. Cacace, E.M. Landau and J.J. Ramsden, The Hofmeister series: salt and solvent effects on interfacial phenomena, Quarterly Reviews of Biophysics 30, 3 (1997), pp. 241–277, 1997 Cambridge University Press, United Kingdom.

A. George, Y. Chiang, B. Guo, A. Arabshahi, Z. Cai, and W. William Wilson, [6] Second Virial Coefficient as Predictor in Protein Crystal Growth, Methods in Enzymology, vol. 276.

Abraham George and W. William Wilson, Predicting Protein Crystallization from a Dilute Solution Property, Acta Cryst. (1994), D50, 361–365, Department of Chemistry, Mississippi State University, Mississippi State, MS, USA.

D. Rosenbaum, P.C. Zamora, and C.R. Zukoski, Phase Behavior of Small Attractive Colloidal Particles, Physical Review Letters, vol. 76, No. 1, Jan. 1, 1996, Department of Chemical Engineering and Beckman Institute of Advanced Study, University of Illinois, Urbana, Illinois, USA.

C. Gripon, L. Legand, I. Rosenman, O. Vidal, M.C. Robert, F. Boué, Lysozyme solubility in $H_2O$ and $D_2O$ solutions: a simple relationship, Journal of Crystal Growth 177 (1997) 238–247, Paris, France.

C. Gripon, L. Legand, I. Rosenman, O. Vidal, M.C. Robert, F. Boué, Lysozyme–lysozyme interactions in under–and super–saturated solutions: a simple relation between the second virial coefficients in $H_2O$ and $D_2O$, Journal of Crystal Growth 178 (1997) 575–584, Paris, France.

C. Gripon, L. Legrand, I. Rosenman, F. Boué, C. Regnaut, Relation Between the solubility and the effective solute–solute interaction fro C60 solutions and lysozyme solutions: a comparison using the sticky hard–sphere potential, Journal of Crystal Growth 183 (1998) 258–268, Paris, France.

Gary L. Gilliland and Michel Tung, Screening for Crystallization Conditions and Robotics, Biological Macromolecule Crystallization Database, Version 3.0: New Features, DAta and the NASA Archive for Protein Crystal Growth Data, Acta Cryst. (1994), D50, 408–413, Center for Advanced Research in Biotechnology of the Maryland Biotechnology Institute and National Institute of Standards and Technology, Rockville, MD, USA.

Cleopas T. Samudzi, Matthew J. Fivash and John M. Rosenberg, Cluster Analysis of the Biological Macromolecule Crystallization Database, Journal of Crystal Growth 123 (1992) 47–58, North–Holland, ABL–Basic Research Program, Frederick Cancer Research and Development Center, National Cancer Institute, Frederick, Maryland, USA.

Robert G. Farr, Jr., Alexander L. Perryman, Cleopas T. Samudzi, Re–clustering the database for crystallization of macromolecules, Journal of Crystal Growth 183 (1998) 653–668, Biochemistry Department, University of Missouri–Columbia, MO, USA.

Daniel Hennessy and Vanathi Gopalakrishnan and Bruce G. Buchanan, Induction of Rules for Biological macromolecule Crystallization, Dept. of Biological Sciences and Crystallography, University of Pittsburgh, Pittsburgh, PA, USA.

Commerical pamphlet "Crystallization Research Tools", graphs of the frequency of successful employment of various crystallizing agents and various pH values that give a feel for the limits on each when contemplating a crystallization screening.

D.F. Rosenbaum, C.F. Zukoski, Protein interactions and crystallization, Journal of Crystal Growth 169 (1996), 752–758, Department of Chemical Engineering, University of Illinois, Urbana, Illinois, USA.

METHOD FOR GROWING CRYSTALS

CROSS-REFERENCE TO RELATED APPLICATION

The present application claims priority based on provisional application Serial No. 60/198,995, filed Apr. 21, 2000.

BACKGROUND OF THE INVENTION

1. Field of the Invention

The present invention generally relates to microbatch crystallization under oil using a high throughput method. Microbatch crystallization under oil requires very low volumes of both a protein and a crystallization cocktail solution. This is critical for a high throughput application where a large number of experiments are being conducted at the same time. Many proteins can be difficult if not impossible to obtain in large quantities and cocktail solutions are costly to produce. According to the present invention, one plate of 1,536 crystallization experiments is set up using as little as 600 µl of protein solution. From this volume, 100 µl of the protein is retrieved at the conclusion of the experiments for use in further studies.

2. Prior Art

A number of investigators have attempted to condense their experiences in the crystal growth laboratory into a list of recipes of reagents that have found success as crystallizing agents. The most used of these is the list compiled by Jancarik, J. and Kim, S.-H. (1991), J. Appl. Cryst. 24, 409–411 which is often referred to as the "sparse matrix sampling" screen. The list is a "heavily biased" selection of conditions out of many variables including sampling pH, additives and precipitating agents. The bias is a reflection of personal experience and literature reference towards pH values, additives and agents that have successfully produced crystals in the past. Commercialization of the sparse matrix screen has led to its popularity; easy and simple to use, it is often the first strategy in the crystal growth lab.

The agents chosen by Jancarik and Kim are designed to maximize the frequency of precipitation outcomes for a broad variety of proteins. They were chosen because in a large percentage of experiments employing them "something happened". This highlights a fundamental difference between the present invention and the approach taken by Jancarik, Kim and their successors. The latter try to identify sets of chemical agents that maximize the probability of inducing precipitation (preferably crystallization) across the board, while the present invention relies on a set of chemical agents with precise patterns of precipitation, patterns that are as diverse as possible among the proteins that constitute the information repository. The fact that the sparse matrix approach does not always work has led to the design of other lists targeted at proteins. These include those by Cudney, R., Patel, S., Weisgraber, K., Newhouse, Y. and McPherson, A. (1994), Acta Cryst. D50, 414–423 directed to nucleic acids, by Berger, I., Kang, C. H., Sinha, N., Wolters, M., and Rich, A. (1996), Acta Cryst. D52, 465–468 directed to other classes of macromolecules, and by Garavito, M. (1991), in "Crystallization of Membrane Proteins", H. Michel (Ed.), CRC Press, pp. 89–105.

The sparse matrix approach is based on unbiased attempts to sample the multi-dimensional space of crystallization parameters. At least 23 parameters have been identified as having had an effect on crystallization outcomes. If one were to attempt a simple, exhaustive two-level experimental design for an unknown protein, i.e., two pH values, two temperatures, two kinds of crystallizing agents, etc., it would require $2^{23}$ or over eight million experiments. Hence the need for sampling.

Carter, C. W. (1997), in Methods in Enzymology 276, 74–99 made major advances in the area of crystal growth by applying partial factorial designs, principally incomplete factorial designs. In these designs, relative levels of important chemical factors are sampled to achieve good coverage and good balance in the sampling. However, incomplete factorial designs are no more than (or no less than) scaffolds upon which the crystal grower must build experiments.

In other words, once the crystal grower has defined the multi-dimensional space which should be sampled, the factorial designer chooses from the large number of possible experiments those that should be executed to insure good coverage of the space identified. The crystal grower must decide upon the important variables to be tested, and the limits on those variables within which to sample. The machinery of factorial design offers no guidance on those issues. Other sampling strategies based on orthogonal arrays by Kingston, R. L., Baker, H. M. and Baker, E. N. (1994), Acta Cryst D50, 429–440 and on random samplings by Shieh, H.-Y., Stallings, W. C., Stevens, A. M., and Stegeman, R. A. (1995), Acta Cryst. D51, 305–310 have been described as well.

A fundamentally different approach to strategic planning of crystallization experiments is one in which physical principles believed to augur well for success are exploited. This class includes the work of Riès-Kautt, M. and Ducruix, A. (1997), Methods in Enzymology 276, 23–59 who have investigated solubility determinants for proteins as a function of pH and pI. In particular, Riès-Kautt, Ducruix and co-workers investigated the Hofmeister series developed by Cacace, M. G., Landau, E. M., and Ramsden, J. J. (1997), Quart. Res Biophys. 30, 241–277 and found that protein solubility follows the series or its reverse, depending on the pH of the experiment and the pI of the protein. Also within this approach are recent advances by George, A., Chiang, Y., Guo, B., Arabshaki, A., Cai, Z., and Wilson, W. W. (1997), Methods in Enzymology 276, 100–109 in the use of light scattering as a predictive tool and by George, A. and Wilson, W. W. (1994), Acta Cryst. D50, 361–365 who have shown that a dilute solution property, the second virial coefficient of the osmotic pressure lowering, falls within a narrow range of values (the "crystallization slot") for solutions conducive to crystallization. Work by Rosenbaum, D., Zamora, P. C., and Zukoski, C. F. (1996), Phys. Rev. Lett. 76, 150–153; Rosenbaum, D. and Zukoski, C. F. (1996), J. Crystal Growth 169, 752–758; Gripon, C., Legrand, L., Rosenman, I., Vidal, O., Robert, M. C., and Boué, F. (1997), J. Crystal Growth 177, 238–247 and 178, 575–584; and Gripon, C., Legrand, L., Rosenman, I., Boué, F., and Regnaut, C. (1998), J. Crystal Growth 183, 258–268 suggest that the second virial coefficient is a fundamentally important determinant of crystallization from aqueous protein solutions.

The final approach to strategic planning tactics is the construction and analysis of the Biological Macromolecule Crystallization Database (BMCD), in which details of macromolecular crystallizations abstracted from the primary literature have been collected. The BMCD was created by Gilliland, G. L., Tung, M., Blakeslee, D. M., and Ladner, J. E. (1994), Acta Cryst. D50, 408–413 and has, over the last decade, grown to include crystallization data on over three thousand crystal entries covering over two thousand distinct macromolecules (Version 3.0). The record structures of the BMCD, while not requiring any particular record to be complete, include entries for the macromolecule, the crystal data, the crystallization conditions, the primary literature references, and a field for comments. These data have been abstracted, where available, from the primary literature and there are entries for every major class of macromolecule (protein, nucleic acid, virus, etc.) that have been studied in the diffraction lab. Each record is a record of success—there are no records describing crystallization experiments that failed to yield crystals. Gilliland has pointed out that the data in the BMCD "have not been verified and the information present in this data set often represents the author's [Gilliland's] interpretation of the literature".

Gilliland was first to analyze the BMCD to develop crystal growth strategies for macromolecules. He showed that ammonium sulfate and polyethylene glycol were favored crystallizing agents and that vapor diffusion was a favored crystallization method. While both observations were part of the common lore of crystal growth, Gilliland used the BMCD to quantitate their use.

Samuzdi and co-workers delved more deeply into the BMCD, looking for general strategies that might be effectively used for smaller sub-populations of the database. The statistical tool they chose to employ was cluster analysis. Using version 1.0 of the BMCD in 1992, Samuzdi, C. T., Fivash, M. J., and Rosenberg, J. M. (1992), J. Crystal Growth 123, 47–58 and version 3.0 in 1998, Farr, R. G., Perryman, A. L., and Samuzdi, C. T. (1998), J. Crystal Growth 183, 653–668 searched for clusters involving the following parameters: molecular weight, macromolecular concentration, pH, temperature, crystallizing agent type, and crystallization method. Focusing on very recent results Samuzdi identified 25 clusters within the BMCD that were judged statistically distinct. Fully a third of the clusters (8 out of 25) were sparsely populated and were, therefore, ignored in further treatment. Clustering identified nucleic acids, protein-nucleic acid complexes and viral assemblies as behaving distinctly in successful crystallizations from the general class of soluble proteins. A further weak distinction between the behaviors of very small proteins and all other proteins was drawn, but apart from the method of crystallization no other single parameter (macromolecular concentration, pH, temperature, crystallizing agent type) was shown to cluster in any significant manner. While Samuzdi reports strategies for the 17 populated clusters, it is virtually impossible on the basis of molecular weight (the only intrinsic property of the macromolecule that could be used as a pointer) to decide which strategy to employ for any particular protein.

Hennessy, D., Gopalakrishnan, V., Buchanan, B. G., Rosenberg, J. M., and Subramanian, D. (1994), Proceedings, Second International Conference on Intelligent Systems for Molecular Biology, ISBM-94, AAAI Press, pp. 179–187 took a different approach. They attempted to use the BMCD Version 1.0 to induce rules for macromolecular crystallization. This so called machine induction is an automatic construction of arguments from the particular to the general which attempts to identify "a disjunctive set of weighted conjunctive rules". Conjunctive rules are of the form IF (A and B and C, etc.) OR IF (D and E and F, etc.), THEN (conclude, do) something. An example of a very simple rule might be: if the crystal habit has the value "plates" then the diffraction limit is under 3.5 Å. Rules are generated in an automatic fashion and then are tested against the data to see if they hold.

In actual applications with databases as small and sparse as the BMCD, the depth of the rules generated is severely limited because their numbers grow exponentially and there are insufficient data to adequately test complicated rules. When the rules outnumber the data, it is difficult to evaluate if one rule is to be preferred over another. To counter this problem, Buchanan incorporated "domain knowledge to guide the induction of rules". Here the domain in question is the crystal growth domain. While the formal techniques employed to introduce "domain knowledge" into the logic are described, it is unclear how they were implemented in detail to limit and guide the rule generation and testing. Buchanan pointed out that the absence of negative results (crystallization failures) in the BMCD severely hampered the search for crystal growth rules. Rules that would be most useful, such as "if you carried out the following crystallization experiment, you would observe the following results" were not induced, suggesting that rule-based approaches to strategy planning would not likely succeed.

Finally, Bob Cudney, owner of Hampton Research, Laguna Hills, Calif., in the commercial pamphlet "Cyrstallizatin Research Tools" has surveyed the BMCD and produced graphs of the frequency of successful employment of various crystallizing agents and of various pH values that give a feel for the limits on each when contemplating a crystallization screening. In combination with formal search techniques such as incomplete factorial designs, the analyses put forth by Cudney are extremely useful.

SUMMARY OF THE INVENTION

In that light, the present invention relates to an integrated decision-support system that aids the crystal grower in devising successful crystallization strategies. The goal is to be able to predict, through analysis of carefully selected sets of precipitation reactions, the key elements of successful crystallization strategies. This strategy is predicated on the principle that successful crystallization strategies employed for similar proteins are the best guide when plotting strategies for new proteins. In other words, the pattern of outcomes in successful precipitation reactions yields the objective measure of similarity for designing new reaction experiments. This requires an objective measure of similarity between successfully grown crystals and those being planned.

This objectivity is provided by the execution, evaluation and binary-encoding of the outcomes of reactions involving hundreds of proteins and precipitating agents. In method and form these precipitation reactions are indistinguishable from microbatch crystallization experiments: solubilized proteins are incubated with agents that have the potential to reduce their solubilities, aggregation and phase separation either does or does not result, and the extent with which it does is assessed visually. The distinction is that the present method is a high throughput process. The many outcomes are then used to develop a set of precipitation reaction indices that allow the crystal grower to efficiently, objectively and quantitatively evaluate the similarity of any two proteins with respect to a physical property intimately connected to crystal growth, namely, solubility.

In that respect, the goal of the present invention is to develop an opening strategy that gets the crystal grower into optimization experimentation quickly. On the basis of a small number of precipitation reactions, i.e., 1,536 precipitation reactions, requiring less than a milligram of protein, taking no more than a few hours to set up and perhaps as little as one day to evaluate, the crystal grower is able to propose the crystallization method of choice, the crystallizing agent, the pH and temperature, and approximate concentration ranges for all solutes. The practical implications are tremendous.

Structural biology is at a point where the floodgates of structure determination are beginning to open. Among methods employed to reveal the details of molecular structure, none rivals single crystal X-ray diffraction for its generality of application, clarity of view, and lack of ambiguity in interpretation. Entry into the diffraction method is via growth of a suitable single crystal of the target macromolecule. The crystal growth problem has repeatedly been identified as the rate-limiting step in macromolecular structure determination.

According to the present invention, experiences with similar crystallization problems, successfully engaged in the past, are the best guide to the solution of new crystallization problems in the future. The present invention, therefore, provides a predictive, objective, quantitative and absolute measure of similarity in experimental outcomes called a "precipitation reaction index." This index is based on the results of 1,536 precipitation reactions between an unknown protein and 1,536 standardized cocktail solutions, and is the link between structural, physical, chemical and biological properties of macromolecules and their behavior in crystallization experiments. In that respect, experimentally determined precipitation reaction indices of known proteins and the unknown protein with the 1,536 standardized cocktail solutions are strongly linked to both crystallization outcomes and to the intrinsic properties of macromolecules. By analyzing three independent types of data (intrinsic properties, precipitation reaction indices, and crystallization strategies), it is believed that previously unsuspected, nontrivial relationships between intrinsic properties and crystallization outcomes will significantly aid the crystal grower in a fundamental understanding of the crystal growth process.

These and other objects of the present invention will become increasingly more apparent to those skilled in the art by reference to the following description and to the appended drawings.

DETAILED DESCRIPTION OF THE PREFERRED EMBODIMENTS

Figure 1:
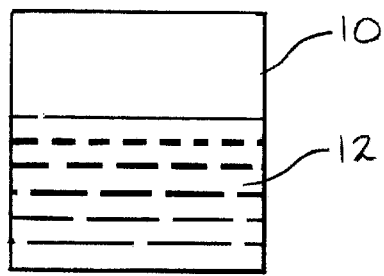
FIGS. 1 to 5 are a schematic sequence of the set up of a single well crystallization experiment according to the present invention.
Figure 2:
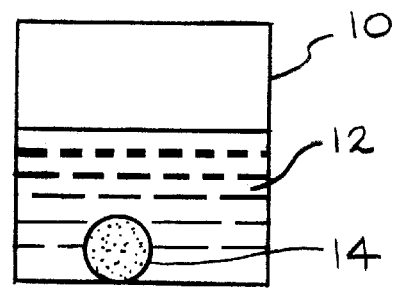

Turning now to the drawings, FIGS. 1 to 5 are a schematic representations of the stages in a microbatch crystallization experiment according to the present invention. The first step begins with a dry, clean and un-filled experiment well 10. As shown in FIG. 1, the well 10 is partially filled with a paraffin oil 12. The paraffin oil 12 has low water permeability and forms a liquid container for the small volume experiment drop which will be added to the oil later. The oil 12 encases the drop, and both prevents evaporation and buffers the drop from thermal variations during the experiment. Next, a drop of a crystallization cocktail 14 (FIG. 2) is added to the oil filled well. The cocktail 14 is used as a chemical means to achieve supersaturation of a protein solution that will be added to the liquid container in the next stage. The chemical component of the cocktail varies and suitable cocktails are selected from salts, organic polymers and buffering agents to regulate pH.

In particular, the cocktails are composed of three parts of unequal size. The list includes: 288 cocktails having 35 inorganic salts in combination with 8 buffers; 1051 cocktails of five poly-ethylene glycols (PEG) or methyl-2,4-pentane-diol in combination with the same 35 salts and 8 buffers as above; and 196 crystallization cocktails commercially available from Hampton Research, Laguna Hills, Calif.

The 35 inorganic salts include: ammonium bromide, ammonium chloride, ammonium nitrate, ammonium phosphate (monobasic), ammonium phosphate (dibasic), ammonium sulphate, ammonium thiocyanate, calcium acetate, calcium chloride, lithium bromide, lithium chloride, lithium sulphate, magnesium acetate, magnesium chloride, magnesium sulfate, magnesium nitrate; manganese sulphate, potassium acetate, potassium bromide, potassium carbonate, potassium chloride, potassium nitrate, potassium phosphate (monobasic), potassium phosphate (dibasic), potassium phosphate (tribasic), potassium thiocyanate, rubidium chloride, sodium bromide, sodium chloride, sodium molybdate, sodium nitrate, sodium phosphate, sodium thiosulfate, zinc acetate, and cobalt sulfate. In the salt/buffer cocktails the salts range in concentration from about 0.35M to about 10.0M, and more preferably from about 0.39M to about 9.68M while in the salt/PEG/buffer cocktails, the salts are uniformly at a 0.1M concentration.

The 8 buffers are 2-(N-morphoholino)-ethanesulfonic acid (MES), tris-(hydroxymethyl)aminomethane (Tris), 3-(cyclohexylamino)-2-hydroxy-1-propanesulfonic acid (CAPS), citrate, N-2-hydroxyethylpiperazine-N'-2-ethanesulfonic acid (HEPES), acetate, 3-(N-morpholino)prpoanesulfonic acid (MOPS), and N-tris(hydroxymethyl)methyl-3-aminopropanesulfonic acid (TAPS). All buffers are at a about 0.2M concentration, and the set spans the pH range of about 4.0 to about 10.0. The polyethylene-glycols are of molecular weight 400, 1000, 4000, 8000, and 20000 Daltons, and they range in concentration from 20% (w/v) to 80% (w/v). The Hampton Research cocktails include Natrix, QuikScreen, and Crystal Screens I and II.

Figure 3:
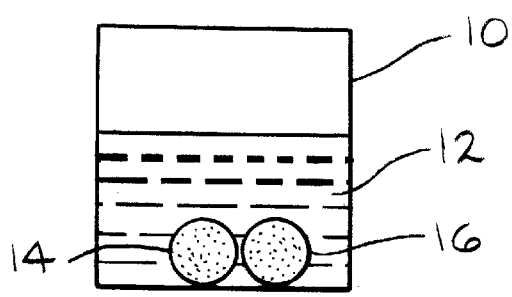
Figure 4:
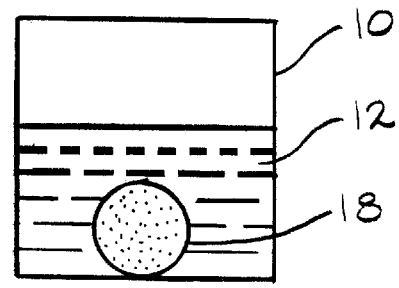
Figure 5:
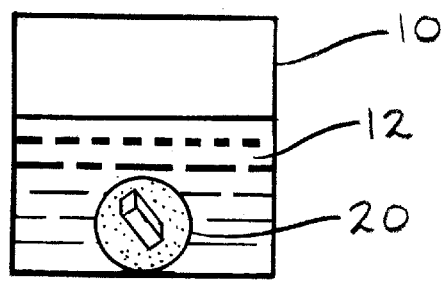

As shown in FIG. 3, a protein solution 16 is delivered to the cocktail drop 14 under the oil 12. In FIG. 4, the two drops merge and co-dilute. If the concentration of protein in the cocktail is sufficiently high, the protein will be supersaturated in the drop. As shown in FIG. 5, this leads to phase separation, potentially leading to crystallization 20 of the protein molecule. The volume of the cocktail drop 14 and protein drop 16 can be varied to produce different ratios and different concentrations of the protein and cocktail solution. This can be used as a means to vary the level of protein saturation in the drop.

Figure 6:
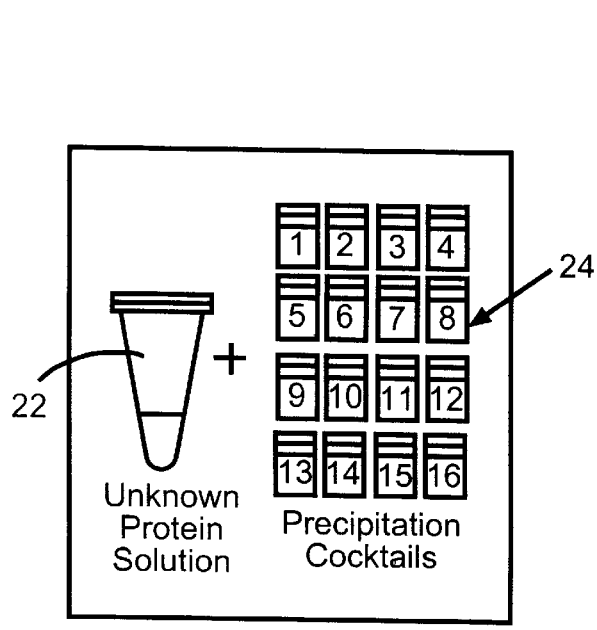
FIG. 6 is a schematic representation of sixteen crystallization experiments for an unknown protein according to the present invention.
Figure 7:
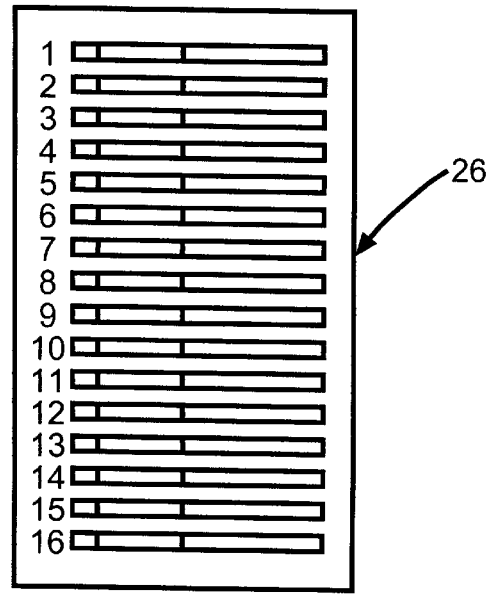
FIG. 7 is schematic representation of the digital images of the crystallization results of the experiments in FIG. 6.
Figure 8:
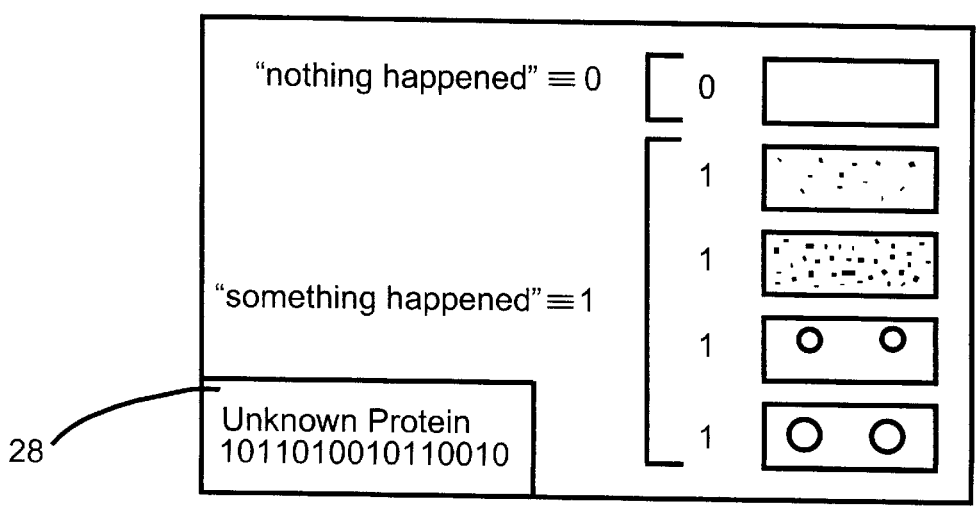
FIG. 8 is a schematic representation of a precipitation reaction index according to the present invention.

As shown in FIG. 6, in order to determine the optimum protocol for growing a crystal of an unknown protein 22, a crystal grower sets up a small number of precipitation reactions, for example sixteen, using sixteen different precipitation cocktails 24. The reactions are incubated for about 24 hours and retrieved for visual evaluation. As shown in FIG. 7, digital images 26 and commentary of the sixteen experiments are recorded. As shown in FIG. 8, the crystal grower then scores the outcomes from a binary menu: "nothing happened" (0) or "something happened" (1) to create a precipitation reaction index 28 as a binary string, e.g. {0010101101001101}. An outcome that falls under the heading "something happened" is a clear, macroscopic indicator of aggregation, a necessary precursor to crystallization. According to the present invention, 1,536 precipitation reactions are preformed.

Figure 9:
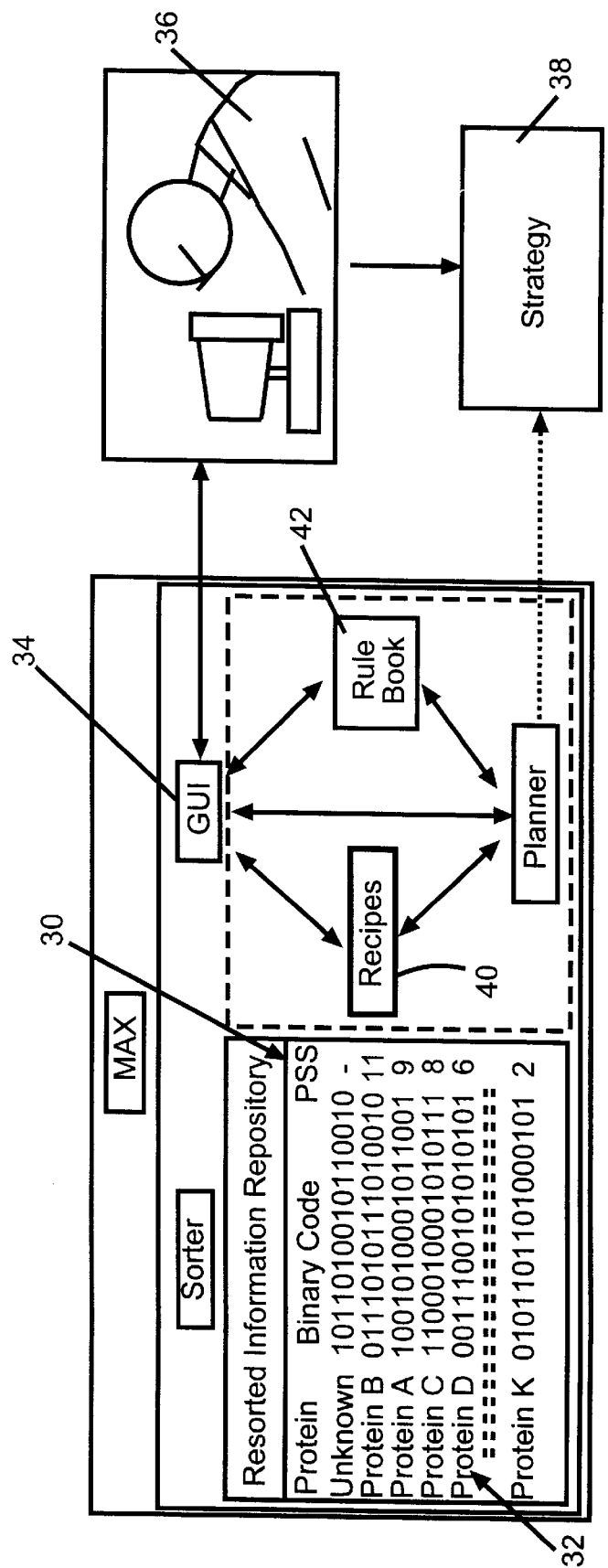
FIG. 9 is a schematic representation of the derivation of a precipitation similarity score and its use in planning additional crystallization experiments for the unknown protein of FIG. 6.

Indices for known (previously crystallized) proteins are in the information repository. So, indications of similarity between an unknown and one of the knowns has to be interpreted as follows: the unknown protein has aggregation properties that are similar to those of a known protein in a set of conditions designed to maximize dissimilarity. Adherence to stringent conditions insures against accidental coincidences in outcomes and for strong empirical relationships relevant to the macromolecular crystallization problem. MAX, an in-house computer program, matches the precipitation reaction index of the unknown with the index of each known to form a set of precipitation similarity scores 30. As shown in FIG. 9, MAX then sorts the repository so that known proteins most similar to the unknown (highest similarity scores) are at the top of the list 32. In a minimalist decision-support system the sorted list is presented via graphical user interfaces 34 to the crystal grower 36, who crafts a new crystallization strategy 38 from recipes 40 and rules 42 that had been employed to successfully crystallize the most similar known proteins.

The following example describes the manner and process of growing crystals according to the present invention, and sets forth the best mode contemplated by the inventors of carrying out the invention, but is not to be construed as limiting.

Preparation of the Cocktail Solutions

A total of 1,536 cocktail solutions were prepared in a minimum volume of 10 ml by creating high concentration stock solutions of salts, PEGs and buffers. These stock solutions were combined with each other and diluted with water to create the final standardized cocktail solutions. The cocktail solutions were given code numbers, such as C##### and were characterized by refractometry, gravimetric density measurement, and pH. The refractive index measurements were used to "fingerprint" the solutions. When the refractive index from a stored solution is compared to the refractive index value for a freshly prepared cocktail solution, a change in the value indicates a variation in the solution composition.

The cocktail solutions were not filtered and did not include any anti-microbial agent as an added preservative. The solutions were stored at 4° C. It was then determined that certain solutions were prone to microbial growth under these storage conditions. These solutions were recreated and stored at −20° C.

Preparation of the 96 Well Cocktail Solution "Grandmother Plates"

The 1,536 cocktail solutions were transferred to labeled Greiner 1.2 ml, 96 well deep well plates (Marsh Biomedical Products) using an Eppendorf Repeater Plus pipet (VWR Scientific) with 10 ml tips (VWR Scientific). The transfer was carried out by pipetting 900 $\mu$l of a particular cocktail solution from a source bottle and delivering it into identical positions on multiple 96 well deep well Greiner plates. Approximately 1 hour was required to fill each 96 well plate. Tape was used to seal each row after filling was completed to minimize evaporative losses. After the plates were completely filled, a piercable cap was used to seal them. The capped plates were then stored at −20° C. This process was repeated to fill replicates of 16 different 96 well "grandmother plates" with a total of 1,536 different cocktail solutions.

Preparation of the 384 Well Cocktail Solution Mother Plates

Groupings of four of the sixteen unique frozen "grandmother plates" were thawed at room temperature and mixed to ensure all of the chemical components of the cocktails were in a homogeneous state. The plates were centrifuged in a Beckman GS-6 centrifuge, 3.8 rotor with microplate carriers (VWR Scientific) to pull all of the solution to the bottom of the wells and pelletize any suspended particles.

The four unique "grandmother plates" (source) were combined into a single 384 well motherplate (destination) using a customized Hydra 96 Microdispenser (Robbins Scientific Corporation). In turn, four of the 384 motherplates were assembled on a tray. The motherplate was a Cycleplate 384 DW CLRLS, which is color-coded to ease organization of the four unique 384 well motherplates (Robbins Scientific Corporation).

A customized Robbins Scientific Hydra 384 robot was used to transfer the cocktail solution to the 384 well motherplate in 20 $\mu$l aliquots. With this method, ten motherplates were filled in less than two hours. Thus, the sixteen 96 well "grandmother plates" were converted into four color-coded 384 well motherplates. These plates were sealed with Cyclefoil and stored frozen at −20° C.

The samples were monitored gravimetrically to check for evaporative losses that may have occurred during storage under a range of temperature conditions from −70° C. to 37° C. The optimal storage temperature based on this analysis was determined to be −20° C.

Preparation of the Experiment Plate-Oil Delivery

The first step in this process was filling each well of the experiment plate with 5 $\mu$l of paraffin oil (Fluka Chemical Corp). The experiment plate was a Greiner 1,536 well microassay plate (Marsh Biomedical Products). Each plate holds 1,536 unique experiments in its 12 $\mu$l volume wells. This oil delivery was accomplished using the customized Robbins Scientific Hydra 384 robot.

To add 5 $\mu$l of paraffin oil to each of the wells on a 1,536 well microassay plate, the following protocol was used. A polypropylene solution tray was filled with paraffin oil to a preset level. The paraffin oil filled tray was placed on the source plate holder of the robot. A 1,536 well plate was placed in the destination plate holder of the robot.

Figure 10:
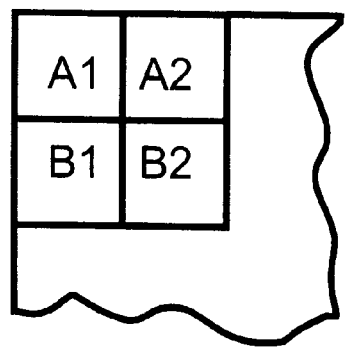
FIG. 10 is a schematic representation of the steps involved in filing a 96 well plate with oil followed by a cocktail additive.

Each of the 384 robot syringes drew up 25 $\mu$l of paraffin oil. Referring now to FIG. 10, the needles were then placed over position A1 of the 1,536 well plate. The plate was raised into position, and the syringes delivered the oil into onequarter of the wells. After a pause to make certain all of the oil was delivered, the stage dropped away from the needles, repositioned itself and delivered to position B1. The process was repeated at positions A2 and B2 until all of the wells were filled with oil.

Preparation of Experiment Plates-Cocktail Delivery

Four unique cocktail-filled 384 well motherplates were removed from −20° C. storage and thawed at room temperature. These plates contained the 1,536 unique cocktail solutions that were set up in each 1,536 well experiment plate. The motherplates were sonicated and vortex mixed to resolubilize any material that precipitated from solution during storage. After the solutions were visually checked for homogeneity, the plates were centrifuged to pelletize any insoluble matter and collect the solution at the bottom of the wells.

A motherplate was placed on the source position of the Hydra 384 robot stage. An oil-filled 1,536 well experiment plate was placed on the destination position of the stage. The stage translated to line up the 384 syringes over the cocktail motherplate. The cocktail solution was withdrawn from the motherplate into the syringe barrels. The positioning stage moved to locate position A1 (FIG. 10) of the 1,536 well oil-filled experiment plate under needle number 1. This aligned the 384 needles in a pattern over every other well on the plate. The needles were positioned such that the tips were just under the top of the oil in each well. The robot then dispensed 0.2 μl of cocktail solution. The robot repeated the delivery portion of the protocol on the remaining oil-filled experiment plates, dispensing 0.2 μl of cocktail to position A1 of each of them. After one-quarter of the cocktail solutions were delivered to the desired number of experiment plates, the protocol was concluded. It took less than one minute to deliver 384 cocktail solutions to each plate.

The second in the series of four 384 well cocktail motherplates was then placed into the source position on the Hydra 384 robot stage. The protocol followed was nearly identical to that used to fill the first quarter of the wells of the oil-filled experiment plate with cocktail solutions except that needle one delivered to position B1 on the experiment plate and delivered to every other well on the 1,536 well plate. Again, the deliveries were made to the same position on multiple destination plates until the run was completed. The process was repeated with the third and fourth 384 well cocktail motherplates delivered at positions A2 and B2, respectively, until the experiment plates contained all of the unique cocktail solutions. A single motherplate containing 20 μl of each cocktail solution contains enough solution to set up nearly 100 experiment plates containing 0.2 microliters of cocktail per well.

At the end of this process, each well of the experiment plates contained 5 μl of paraffin oil and 0.2 μl of one of 1,536 unique cocktail solutions. The plates were centrifuged to make certain all of the cocktail drops were seated at the bottom of the wells. This prevents cross-contamination when delivering protein solution in the next stage of the experiment, aids in focusing the drop images on the reader table when the results of crystallization are later visibly ascertained, and prevents the drops from drying out due to being too close to the surface of the oil. The plates were then stored for later use.

Preparation of Experiment Plates—Protein Delivery

A protein stock solution must have a minimum volume of 600 μl for 0.2 μl/protein solution/experiment drop or 1,000 μl for 0.5 μl/protein solution/experiment drop. The protein stock solution was ideally prepared in distilled deionized water for minimum interaction between the protein buffer and the cocktail solutions. The starting protein stock concentration in a microbatch experiment is diluted by one-half when the protein stock is combined with the cocktail solution (assuming equal volumes of both solutions are added to the experiment plate). For this reason, higher concentrations of protein solution were generally required to set up a successful microbatch crystallization experiment than are required to set up crystallization experiments using a prior art vapor diffusion method.

The protein solution of appropriate volume was initially placed into a microcentrifuge tube. The solution was centrifuged to pellet out particulates. The protein was then manually delivered to 96 wells of a Microscreen plate (Robbins Scientific Corporation) using an Eppendorf Repeater Plus Pipetter with 0.2 ml tips (VWR Scientific). It took less than 2 minutes to deliver protein to all of the wells in the plate. To set up 0.5 μl protein drops in the experiment, 10 μl of protein solution was required per well. To set up 0.2 μl protein drops in the experiment, 6 μl of protein solution was required per well.

Figure 11:
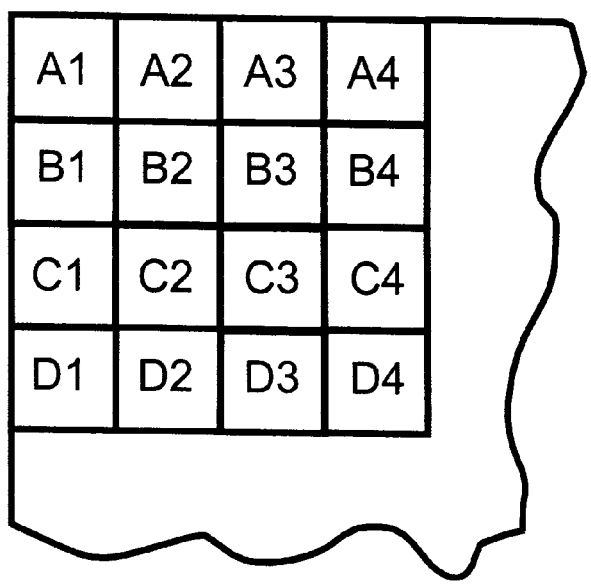
FIG. 11 is a schematic representation of the steps involved in filing the 96 well plate of FIG. 10 with a protein solution to provide a crystallization experiment according to the present invention.

The plates were sealed using Cyclefoil and centrifuged to make certain all of the protein solution was at the bottoms of the wells. The foil seal was then removed from the protein plates and the plates were placed on the robot in the source plate position. The 1,536 well experiment plate containing the oil and cocktail solutions was placed in the destination position on the robot stage. For a 0.5 μl protein drop experiment, the robot drew up a 5 μl air gap and 9.5 μl of protein. The stage positioned the needles just under the oil in the experiment plate and delivered 0.5 microliters of protein to position A1 of the 1,536 well plate. The delivery proceeds in the order of A1-D1, A2-D2, A3-D3, A4-D4 (FIG. 11) for a total of 16 deliveries to the experiment plate. This took about 4.5 minutes for the robot to complete.

The experiment plate was centrifuged to combine the cocktail and protein drops and to make certain all of the drops rested on the bottom of the well under the paraffin oil. The merged and co-diluted cocktail solution and protein drop in each well were then incubated at a temperature of about 4° C. to about 35° C. for about 24 hours to about one month. The remaining protein in the Microscreen 96 plate was removed using a Pipetman P-100 and pooled in a microcentrifuge tube. The typical recovery was 100 μl of protein.

Plate Imaging System

A plate imaging system was developed at the Hauptman-Woodward Institute, Buffalo, N.Y. to digitally record the results of each experiment in a 1,536 well plate. A custom built large travel imaging stand made of stainless steel supports the imaging system. The stand supports a telecentric zoom video system with a high resolution, mega pixel CCD camera on a fine focus (Brook-Anco Corp). The video system records individual wells of an experiment plate. The stand can accommodate twenty-eight experiment plates, each resting on a piece of plate glass with a custom Lexon framework to hold the plates in place. The plate glass and framework are mounted to a 30"×30" Daedal X-Y Precision 2 axis table with a 4 axis indexing card (Ross Equipment Co., mc). The lighting for the image capture process is provided by a heat filtered Fostec light source and pad (Brook-Anco Corp). The video camera feeds into a Flashpoint NT framegrabber (Brook-Anco Corp). The table motion and image capturing is computer-controlled through an in-house program which allows the user to define the image size that is captured, name the plate and define plate position on the table. The images are recoded and then saved to a file. The results of each experiment are digitally recorded at a rate of 2 plates per hour at a resolution of 640×480.

MacroScope

MacroScope is a program written in-house at the Hauptman-Woodward Institute to examine the results of the 1,536 well plate's crystallization experiments. Examining the results of the experiment under a microscope is extremely difficult. The program takes images from a folder containing the images of a single plate and allows the user to view the results grouped the way they would appear in the original 96 well "Grandmother Plates". This is a rational order where the cocktails are organized according to single parameter variation. This may be an increase in concentration of a precipitating agent, a variation of pH or some similar variation. The program displays the images in sixteen 96 well plates. The experiments appear as 96 thumbnail images. The patterns of precipitation and crystallization are very plain to view by anyone familiar with protein crystallization. By clicking a checkbox next to each thumbnail image the cocktail conditions for those experiments are saved to a text file for later viewing. All of the check-boxed thumbnails can be viewed side by side for comparison.

The results were encoded "nothing happened" by zero (0), and "something happened" by one (1), to provide a precipitation reaction index as a binary string with a single character for each precipitation reaction. For example, in a case where there are four precipitation cocktails, there could be $2^4=16$ distinct outcomes for any particular protein. A precipitation reaction index equal to (0100) implies that upon incubation of the protein with precipitation cocktail #2 "something happened" while upon incubation with cocktails #1, #3 and #4 "nothing happened." The index captures the results of the precipitation reactions in a compact, sortable form, with a single bit representing each precipitation reaction undertaken. The definition of the index flexibly covers any number of precipitation reactions per protein.

According to the present invention, a precipitation similarity score is derived from the precipitation reaction indices for two proteins by comparing and summing the bits that have identical values for both reaction indices. For example, the similarity score for two proteins with reaction indices {0010} and {1010} is 3-the last three bits in the two reaction indices are identical. A particular protein can have an identical similarity score with two other proteins without the latter having to have the same precipitation reaction indices. For example, if the reaction indices of an unknown protein and two known proteins are {0010}, {1010} and {0011}, respectively, the similarity scores for the two pairings of unknown with the known are both 3, while the pairing of the two knowns with each other has a similarity score of 2. High values of the precipitation similarity score indicate that two proteins behave similarly in precipitation reactions; the implications are that successful crystallization strategies for one may be of relevance for the other. The summing of the number of bits for which two precipitation reaction indices have identical values (both are 0 or both are 1) erases reference to particular precipitation cocktails, i.e., each precipitation reaction outcome contributes equally to the similarity score.

The precipitation similarity score involves precipitation reaction indices for any pair of proteins. With 16 precipitation reactions, the reaction indices of two proteins can have zero coincidences, sixteen coincidences or something between those extremes; i.e., the similarity score can range from 0 to 16. There are similarity scores that characterize an unknown with respect to each known in the repository. The set of precipitation similarity scores (one for each pairing of an unknown with a known) represents a way to objectively order the proteins in the information repository. Proteins in the sorted list having the most similar precipitation reaction score are at the top of the list and those which are the least similar are at the bottom. The similarity score for a fixed number of precipitation reactions is an absolute measure of precipitation outcome similarity.

Then, based on the precipitation similarity score, a strategy is devised for growing crystals of the unknown protein. In that respect, on the basis of a small number of precipitation reactions, requiring less than a milligram of protein, taking no more than a few hours to set up and perhaps as little as one day to evaluate, it is possible to propose the crystallization method of choice, the crystallizing agent, the pH and temperature, and approximate concentration ranges for all solutes to successfully grow crystals of the unknown protein.

It is appreciated that various modifications to the present inventive concepts described herein may be apparent to those of ordinary skill in the art without disporting from the spirit and scope of the present invention as defined by the herein appended claims.

What is claimed:

1. A method for growing crystal, comprising the step of:
   a) setting up at least three crystallization experiments comprising filling an oil in at least three crystallization wells, providing a cocktail solution in the wells and providing a solution of at least one unknown protein and at least two known proteins in separate ones of the wells such that the cocktail solution and the protein solutions in the oil merge and co-dilute to form the at least three experiments;
   b) incubating the crystallization experiments;
   c) visually inspecting the results of the crystallization experiments to determine if crystallization has occurred;
   d) scoring the results of the crystallization experiments zero (0) if no crystallization occurred and one (1) is something happened to provide a precipitation reaction index;
   e) deriving a precipitation similarity score from the precipitation reaction indices of the known protein with that of the unknown proteins to determine which of the known proteins the unknown protein is most similar to; and
   f) developing a strategy based on results of the precipitation similarity score of the unknown protein with that of the known proteins to devise a new crystallization experiment for the unknown protein.

2. The method of claim 1 wherein the oil is a paraffin oil.

3. The method of claim 1 wherein cocktail solutions are selected from the group consisting of inorganic salts, organic polymers and buffering agents.

4. The method of claim 3 including selecting the inorganic salts from the group consisting of ammonium bromide, ammonium chloride, ammonium nitrate, ammonium phosphate (monobasic), ammonium phosphate (dibasic), ammonium sulphate, ammonium thiocyanate, calcium acetate, calcium chloride, lithium bromide, lithium chloride, lithium sulphate, magnesium acetate, magnesium chloride, magnesium sulfate, magnesium nitrate; manganese sulphate, potassium acetate, potassium bromide, potassium carbonate, potassium chloride, potassium nitrate, potassium phosphate (monobasic), potassium phosphate (dibasic), potassium phosphate (tribasic), potassium thiocyanate, rubidium chloride, sodium bromide, sodium chloride, sodium molybdate, sodium nitrate, sodium phosphate, sodium thiosulfate, zinc acetate, and cobalt sulfate.

5. The method of claim 4 including combining at least one of the inorganic salts with either polyethylene glycol or methyl-2,4-pentanediol.

6. The method of claim 3 including providing the inorganic salts in a concentration of about 0.35M to about 10.0M.

7. The method of claim 3 including selecting buffer from the group consisting of 2-(N-moropholino)-ethanesulfonic acid (MES), tris-(hydroxymethyl)aminomethane (Tris), 3-(cyclohexylamino)-2-hydroxy-1-propanesulfonic acid (CAPS), citrate, N-2-hydroxyethylpiperazine-N'-2-ethanesulfonic acid (HEPES), acetate, 3-(N-morpholino) prpoanesulfonic acid (MOPS), and N-tris(hydroxymethyl) methyl-3-aminopropanesulfonio acid (TAPS).

8. The method of claim 7 including providing the buffers at a concentration of about 0.2M.

9. The method of claim 7 including providing the buffers at a pH range of about 4.0 to about 10.0.

10. The method of claim 7 including providing the polyethylene glycol having a molecular weight selected from the group consisting of 400, 1,000, 4,000, 8,000 and 20,000 Daltons.

11. The method of claim 7 including providing the polyethylene glycol ranging in concentration from about 20% (w/v) to about 80 (w/v).

12. The method of claim 3 including providing the cocktails as commercially available compounds.

13. The method of claim 1 wherein the crystallization experiment is incubated for at least 24 hours.

14. The method of claim 1 wherein the crystallization experiment is incubated at a temperature of about 4° C. to about 35° C.

15. The method of claim 1 further including recording a digital image and commentary regarding the results of the crystallization experiments.

16. The method of claim 15 including recording the digital image using a CCD camera.

17. The method of claim 1 including performing 1,536 crystallization experiments on the unknown protein.

18. The method of claim 1 including summing the number of bits for the precipitation reaction indices of the unknown protein and of the known protein to derive the precipitation similarity score.

19. The method of claim 1 including characterizing the cocktail solution by at least one of a refractory measurement, a gravimetric density an a pH.

* * * * *